US007232907B2

(12) United States Patent
Hayler et al.

(10) Patent No.: US 7,232,907 B2
(45) Date of Patent: Jun. 19, 2007

(54) PROCESS FOR PRODUCTION OF NAPHTHYRIDINE-3-CARBOXYLIC ACID DERIVATIVES

(75) Inventors: John David Hayler, Tonbridge (GB); Hoon Choi, Taejon (KR); Sungwook Cho, Taejon (KR)

(73) Assignee: LG Life Sciences Limited (KR)

( * ) Notice: Subject to any disclaimer, the term of this patent is extended or adjusted under 35 U.S.C. 154(b) by 486 days.

(21) Appl. No.: 10/692,640

(22) Filed: Oct. 24, 2003

(65) Prior Publication Data
US 2005/0176961 A1 Aug. 11, 2005

Related U.S. Application Data

(63) Continuation of application No. 10/070,281, filed as application No. PCT/GB00/03366 on Sep. 1, 1999, now abandoned.

(30) Foreign Application Priority Data
Sep. 3, 1999 (GB) ................................ 9920917.3

(51) Int. Cl.
*A61K 31/4745* (2006.01)
*C07D 471/02* (2006.01)
(52) U.S. Cl. .................................... 546/123
(58) Field of Classification Search ................ 546/123
See application file for complete search history.

(56) References Cited

U.S. PATENT DOCUMENTS

| 5,633,262 | A | 5/1997 | Hong et al. |
|---|---|---|---|
| 5,776,944 | A | 7/1998 | Hong et al. |
| 5,869,670 | A | 2/1999 | Hong et al. |
| 5,962,468 | A | 10/1999 | Hong et al. |
| 6,307,059 | B1 | 10/2001 | Chang et al. |

FOREIGN PATENT DOCUMENTS

| EP | 0 058 614 A1 | 8/1982 |
|---|---|---|
| EP | 0 183 129 A1 | 6/1986 |
| EP | 0 266 576 | 5/1988 |
| EP | 0 183 129 B1 | 8/1989 |
| EP | 0 326 891 | 8/1989 |
| EP | 0 541 086 A1 | 5/1993 |
| EP | 0 688 772 A | 12/1995 |
| EP | 0 688 772 A1 | 12/1995 |
| EP | 0 805 156 A1 | 11/1997 |
| EP | 0 688 772 B1 | 5/1999 |
| JP | 01 100165 A | 4/1989 |
| JP | 03 056479 A | 3/1991 |
| JP | 06-73056 A1 | 3/1994 |
| WO | WO 91/02526 A1 | 3/1991 |
| WO | WO 92/10191 A1 | 6/1992 |
| WO | WO 96/39406 A1 | 12/1996 |
| WO | WO 97/07098 A1 | 2/1997 |
| WO | WO 97/36874 A1 | 10/1997 |
| WO | WO 98 42705 A | 10/1998 |
| WO | WO 98/42705 A1 | 10/1998 |
| WO | WO 99/44991 A1 | 9/1999 |
| WO | WO 99/61420 A1 | 12/1999 |
| WO | WO 00/17199 A1 | 3/2000 |
| WO | WO 01/00209 A1 | 1/2001 |
| WO | WO 01/15695 A1 | 3/2001 |
| WO | WO 01/17961 A2 | 3/2001 |
| WO | WO 01/18002 A1 | 3/2001 |
| WO | WO 01/21176 A1 | 3/2001 |
| WO | WO 01/68649 A1 | 9/2001 |
| WO | WO 02/18336 A1 | 3/2002 |

OTHER PUBLICATIONS

M-J. Ahn, et al., "Effect of a New Fluoroquinolone LB20304a on Microflora of Caecum in Mice", Yakhak Hoeji (Yakhak Hoechi) vol. 40, No. 3, pp. 343-346 (1996).
M-J. Ahn, et al, "Post-Antibiotic Effect of LB20304, A New Quinolone Antibiotic", Yakhak Hoeji (Yakhak Hoechi) vol. 40, No. 3, pp. 347-350 (1996).
M-J. Ahn, et al., "InVivo Efficacy of LB20304a against Experimental Respiratory Tract Infection in Mice", Yakhak Hoeji (Yakhak Hoechi) vol. 40, No. 4, pp. 438-441 (1996).
CS Cooper et al, J. Med. Chem, 35, 1992, 1392-1398.
G. Cormican, "Comparative Antimicrobial and Spectrum Activity of LB20304a, a New Fluoronated Naphthyridone Compound", *Abstracts of the 36th ICAAC*, 109 Abst F53 (1996).
MG Cormican et al, "Antimicrobial Activity and Spectrum of LB20304, a novel Fluoronaphthyridone", *Antimicrobial Agents and Chemotherapy*, Jan. 1997, 41, 204-211.
JM Domagala et al, J. Med. Chem., 31, 1988, 991-1001.
JM Domagala et al, J. Med. Chem., 34, 1991, 1142-1154.
C. Yong Hong, et al., "Novel Fluoroquinolone Antibacterial Agents Containing Oxime-Substituted (Aminomethyl) pyrrolidines: Synthesis and Antibacterial Activity of 7-(4-(Aminomethyl)-3-(methoxyimino) pyrrolidin-1-yl)-1-cyclopropyl-6-fluoro-4-oxo-1,4-dihydro [1,8] naphthyridine-3-carboxylic Acid (LB20304)", *J. Med. Chem.*, 40(22), pp. 3584-3593 (1997).
M-Y Kim et al., "In vitro activities of LB20304, a new Fluoroquinolone", *Arch. Pharm. Res.*, 1996, 19(1), 52-59.
J-H. Kwak, "Antimicrobial Activities of LB20304a, a New Quinolone Antibiotic", *The Journal of Applied Pharmacology* (4) pp. 378-384 (1996).
F. Marco, et al., "Antimicrobial Activity of LB20304, a Fluoronaphthyridone, Tested Against Anaerobic Bacteria, *J. Antimicrobial Chemother* vol. 40, No. 4, pp. 605-607 (1997).
J-I Oh et al, "In vitro and in vivo evaluations of LB20304, a new Fluoroquinolone", *Antimicrobial Agents and Chemotherapy*, Jun. 1996, 40(6), 1564-1568.

(Continued)

*Primary Examiner*—Kamal A. Saeed
(74) *Attorney, Agent, or Firm*—Finnegan, Henderson, Farabow, Garrett & Dunner LLP

(57) ABSTRACT

A process for the production of naphthyridine-3-carboxylic acid derivatives of formula (I) having antibacterial activity.

17 Claims, No Drawings

OTHER PUBLICATIONS

K.-S. Paek et al., "Factors effecting in vitro activity of LB20304, a new fluoroquinolone", *Arch. Pharm. Res.*, 1996, 19(2), 143-147.

K.-S. Paek et al., "Bactericidal activities of LB20304, a new Fluoroquinolone", *Arch. Pharm. Res.*, 1996, 19(4), 317-320.

M-K. Seo, "Pharmacokinetics of LB20304, a New Fluoroquinolone, in Rats and Dogs", *Arch. Pharm. Res.* vol. 19, No. 5, pp. 359-367 (1996).

M-K. Seo et al., "High Performance Liquid Chromatographic Assay of a New Fluoroquinolone, LB20304, in the Plasma of Rats and Dogs", *Arch. Pharm. Res.* vol. 19, No. 6, pp. 554-558 (1996).

Patent Abstracts of Japan, vol. 015, No. 202 (C-0834), May 23, 1991 (JP03056479A, Mar. 12, 1991).

SB-265805, A Potent New Quinolone, 38th Annual Interscience Conference on Antimicrobial Agents and Chemotherapy, ICAAC, San Diego Convention Centre, 105-F Poster Session, New Fluoroquinolones II, Sep. 26th 1998: cover page, contents page and Abstract Nos. F-087 through F-106.

PROCESS FOR PRODUCTION OF NAPHTHYRIDINE-3-CARBOXYLIC ACID DERIVATIVES

This application is a continuation of U.S. patent application Ser. No. 10/070,281 filed May 21, 2002 now abandoned; which is a national stage filing under 35 U.S.C. § 371 of PCT International Application PCT/GB00/03366, filed Sep. 1, 1999.

The present invention relates to a novel process for the production of pharmaceutically active compounds, for example, quinolone carboxylic acid derivatives having antibacterial activity.

EP 688772 discloses novel naphthyridine carboxylic acid derivatives having antibacterial activity, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of the formula:

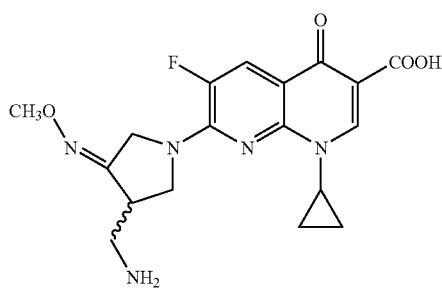

WO 98/42705 discloses (R,S)-7-(3-aminometbyl-4-syn-methoxyiminopyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

EP 688772 discloses a process for the production of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid which comprises the reaction of 7-chloro-1-cyclopropyl-6-fluoro-4-oxo-1,4-dihydro-1,8-naphthyridine-3-carboxylic acid and 4-aminomethyl-3-methoxyiminopyrrolidinium ditrifluoroacetate in the presence of 1,8-diazabicyclo[5.4.0]undec-7-ene using dry acetonitrile as solvent. PCT/KR99/00099 (published after the priority date of the present application) discloses the same process using 4-aminomethyl-3-methoxyiminopyrrolidinium dihydrochloride.

The present invention relates to an improved process for the production of quinoline carboxylic acid derivatives having antibacterial activity.

Thus according to the invention there is provided a process for the production of a compound of formula (I), or a pharmaceutically acceptable salt and/or hydrate thereof:

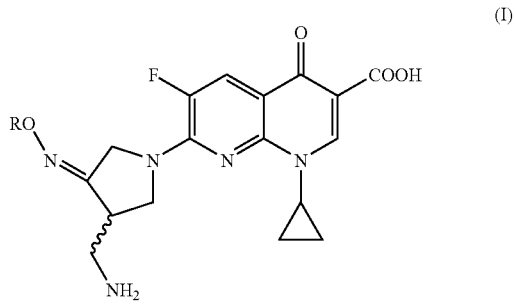

wherein R is $C_{1-4}$ alkyl or $C_{1-4}$ haloalkyl, which comprises reaction of a compound of formula (II):

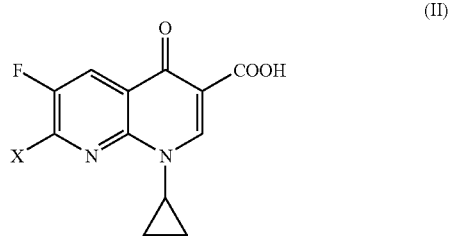

wherein X is a leaving group; with a compound of formula (III):

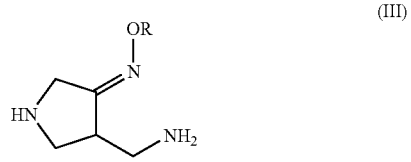

wherein R is as defined for formula (I), or a salt thereof; in the presence of a base and an aqueous solvent;
and optionally forming a pharmaceutically acceptable salt and/or hydrate thereof.

Suitable aqueous solvents for use in the process according to the invention include aqueous acetonitrile and aqueous alcohols, e.g. aqueous $C_{1-6}$ alkyl alcohols such as aqueous ethanol; however the preferred solvent is water.

When the solvent used for the process is a mixed solvent any ratio of solvents may be used, for example when the solvent is aqueous acetonitrile a ratio of between 0.7 and 1.4 acetonitrile:water may be used, preferably 1:1 acetonitrile:water.

The reaction is preferably performed in greater than 1 volume of solvent based on the compound of formula (II), for example 10 volumes of solvent.

The reaction is preferably performed using an excess of the compound of formula (III) to the compound of formula (II), for example between 1.01 and 1.08 mole equivalents of the compound of formula (III), preferably 1.05 mole equivalents.

The reaction is preferably performed at a temperature between ambient and 100° C., for example between ambient and about 60° C.

Suitable bases for use in the process of the invention include organic bases such as triethylamine, diisopropylamine, pyridine, N,N-dimethylaniline, N,N-dimethylaminopyridine, 1,8-diazabicyclo~5.4.0]undec-7-ene and 1,4-diazabicyclo~2.2.2joctane, and tetraalkylammonium hydroxides, e.g. a tetra$C_{1-6}$alkyl alkylammonium hydroxide such as tetrabutylammonium hydroxide or tetramethylammonium hydroxide. Inorganic bases such as sodium and potassium hydrogen carbonate, sodium and potassium hydroxide and sodium and potassium carbonate may also be used.

The base is preferably triethylamine.

Suitably between 3.2 and 3.8 mole equivalents of base are used based on the compound of formula (II), preferably 3.4 mole equivalents of base are used. When the base is a tetraalkylammonium hydroxides then the process may use less than 3 equivalents, e.g. about 2.6 equivalents, of the base.

Suitable leaving groups X in the compound of formula (II) include halogens, particularly chloro, other suitable leaving groups will be apparent to those skilled in the art.

The compound of formula (III) is preferably in the form of the dimethanesulfonate salt, e.g. 4-aminomethyl-3-methoxyiminopyrrolidinium dimethanesulfonate. Other salts of the compound of formula (III) include the hydrochloride, trifluoroacetate and sulfate salts.

Dimethanesulfonate salts of the compound of formula (III) may be produced by a process comprising reaction of a compound of formula (IV):

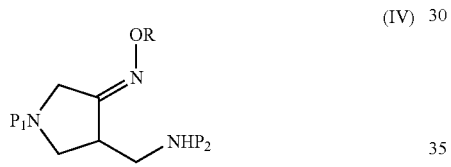

(IV)

wherein R is as defined for formula (I) and $P_1$ and P2, which may be the same or different, are amino protecting groups, with methanesulfonic acid.

Suitable protecting groups $P_1$ and $P_2$ include any suitable amino protecting groups which are removable by treatment with methanesulfonic acid. The preferred protecting group for both $P_1$ and $P_2$ is t-butoxycarbonyl.

The reaction of the compound of formula (II) and methanesulfonic acid is suitably carried out at a temperature between about 10° C. and about 50° C., more preferably at a temperature of 40–45° C.

The amount of methanesulfonic acid used to effect the deprotection of the compound of formula (II) is suitably 2 to 4 equivalents. For example, 2.4 equivalents, suitably used at a temperature of between 35° C. and 40° C.; or 3 equivalents, suitably used at ambient temperature. More preferably 2.5 equivalents used at a temperature of 40–45° C.

The reaction is suitably carried out in a solvent, for example, an alcohol such as methanol, ethanol, isopropanol, or n-propanol, dichloromethane, acetonitrile, acetone, methyl iso-butyl ketone, DME, THF, tert-butylmethyl ether, dioxane or ethyl acetate or a mixture of any of these. The solvent is preferably methanol. Suitably, up to 10 equivalents by volume of solvent may be used, e.g. about 4 equivalents.

The compounds of formula (II), (III) and (IV) may be prepared by the processes described in U.S. Pat. No. 5,633,262, EP 688772 and PCT/KR99/00099.

The compound of formula (I) produced according to the invention is preferably (R,S)-7-(3-aminomethyl-4-syn-methoxyimino-pyrrolidin-1-yl)-1-cyclopropyl-6-fluoro-4-oxo-1,4-dibydro-1,8-riaphthyridine-3-carboxylic acid methanesulfonate or a hydrate thereof, preferably the sesquihydrate, as disclosed in WO 98/42705. The methanesulfonate and hydrates thereof may be synthesised from the free acid as described in WO 98/42705 and WO 00/17 199.

The process of the invention has the advantages that it produces drug substance of superior quality compared to the known process using dry acetonitrile as solvent. In addition the use of an aqueous solvent is more cost effective and may offer environmental advantages.

All publications, including but not limited to patents and patent applications, cited in this specification are herein incorporated by reference as if each individual publication were specifically and individually indicated to be incorporated by reference herein as though fully set forth.

The invention is illustrated by the following examples. However, it should be understood that the examples are intended to illustrate but not in any manner limit the scope of the invention.

EXAMPLE 1

Synthesis of 4-aminomethyl-3-methoxyiminopyrrolidinium dimethanesulfonate

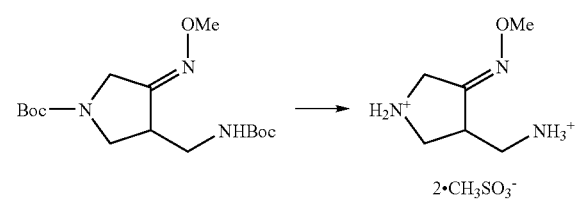

A solution of 1-(N-t-butoxycarbonyl)-4-(t-butoxycarbonylaminomethyl) pyrrolidin-3-methoxime (100 g) in methanol (660 mL) at 15–20° C. under nitrogen was treated with methanesulfonic acid (56.4 mL) over 5 min keeping the temperature below 30° C. The solution was stirred at 20–25° C. for 16–20 hrs. During this time the product precipitated forming a thick suspension. The product was isolated by filtration, washed with methanol (165 ml) and dried under vacuo at 25° C. to give the title compound 84 g (86%).
m.p. 189–193° C.;
m/z: 144 (M+H)$^+$.
$^1$H NMR (400 MHz, d$_6$-DMSO) δ: 9.27, (2H, brs), 7.95 (3H, brs), 4.01 (1H, d), 3.92 (1H, d), 3.87 (3H, s), 3.69 (1H, m), 3.26 (2H, m), 3.26 (2H, m), 3.15 (1H, m), 3.08 (1H, m), 2.39 (6H, s);
Analysis: C, 28.64%, H, 6.25%, N, 12.46%; $C_8H_{21}N_3O_7S_2$ requires C, 28.65%, H, 6.31%, N, 12.53%.

EXAMPLE 2

Synthesis of 4-aminomethyl-3-methoxyiminopyrrolidinium dimethanesulfonate

A solution of 1-(N-t-butoxycarbonyl)-4-(t-butoxycarbonylaminomethyl) pyrrolidin-3-methoxime (100 g) in methanol (400 mL) at 20° C. under nitrogen was treated with methanesulfonic acid (47 mL, 70 g, 2.5 equiv) over 15 min keeping the temperature below 25° C. The solution was heated to 40–45° C. over 30 mins and maintained at this temperature for 4–5 hrs. During this time the product precipitated forming a thick suspension. The crude product was isolated by filtration under nitrogen and washed with methanol (200 mL). The crude product was suspended in methanol (4 volumes, approx. 360 mL) and heated to reflux for 1 hr. After cooling to 20° C. the suspension was stirred for 1 hour. The product was filtered, washed with methanol (2 volumes, approx. 180 ml) and dried under vacuum at 40° C. to give the title compound 73.8 g (78%). Characterising data were consistent with a standard sample of the title compound.

EXAMPLE 3

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid Triethylamine (5.1 ml) was added to 7-chloro-1-cyclopropyl-6-fluoro-4-oxo-1,4-dihydro-1,8-naphthyridine-3-carboxylic acid (3.05 g) in water (25 ml) at 15–20° C. and the mixture stirred for 20 min. 4-Aminomethyl-3-methoxyimino-pyrrolidinium dimethanesulfonate (3.86 g) was added, followed by water (5 ml), and the mixture stirred at 20–25° C. for 17¾ hours. The resulting product was filtered and the cake washed with water (30 ml) followed by ethanol (30 ml) and dried under vacuum at 50° C. to give the title compound as a white solid (4.23 g). (102% as is, 86% on assay). Characterising data were consistent with a standard sample of the title compound.

EXAMPLE 4

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid Triethylamine (34 ml) was added to 7-chloro-1-cyclopropyl-6-fluoro-4-oxo-1,4-dihydro-1,8-naphthyridine-3-carboxylic acid (20.17 g) in a mixture of acetonitrile (100 ml) and water (100 ml) at 15–20° C. and the mixture stirred for 30 mm. 4-Aminomethyl-3-methoxyiminopyrrolidinium dihydrochloride (18.9 g) was added, followed by water (5 ml), and the mixture stirred at 20–25° C. for 23¼ hours. The resulting product was filtered and the cake washed with ice-cold 1:2 acetonitrile:water (100 ml) followed by acetonitrile (100 ml), air dried, then dried under vacuum, at ambient temperature, to give the title compound as a fawn solid (26 g). (94% as is, 78.8% on assay). Characterising data were consistent with a standard sample of the title compound.

EXAMPLE 5

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid A 40% solution of tetrabutylammonium hydroxide in water (15 ml, 23 mmol) was added to a mixture of 7-chloro-1-cyclopropyl-6-fluoro-4-oxo-1,4-dihydro-1,8-naphtbyridine-3-carboxylic acid (2.5 g, 8.8 mmol) and 4-aminomethyl-3-methoxyiminopyrrolidinium dimethanesulfonate (3.12 g, 9.3 mmol) in water (8 ml) at 20–25° C. and the mixture stirred for 24 hours. The resulting product was filtered and the cake washed with water (25 ml) followed by ethanol (25 ml) and dried under vacuum at 50° C. to give the title compound as a white solid (3.47 g). Characterising data were consistent with a standard sample of the title compound.

EXAMPLE 6

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate A solution of methanesulfonic acid (0.33 g, 3.43 mmol) in dichloromethane (1 ml) was added to a suspension of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (1.5 g at 89.9% purity, 3.46 mmol) in a mixture of dichloromethane (23.2 ml) and ethanol (2.7 ml) at 30° C. The mixture was stirred at 30° C. for 3 hours then cooled to 20° C. and filtered. The cake was washed with dichloromethane (20 ml) and dried at 50° C. under vacuum to give the title compound (1.71 g) (102% as is, 91% on assay). Characterising data were consistent with a standard sample of the title compound.

EXAMPLE 7

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesciuihydrate (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate (27.5 g at 91% purity, 51.4 mmol) was stirred in a mixture of isopropanol (150 ml) and water (75 ml) and heated until a clear solution was obtained (52° C.). The solution was cooled to 34° C. and seed crystals of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate added. The resulting suspension was allowed to cool to 25° C. over 1 hour and stirred for 18 hours. The slurry was cooled to 0–4° C., stirred for 2 hours, then filtered and the cake washed with isopropanol (30 ml). The product was sucked dry for 2 hours and then further dried at 50° C. under vacuum. The dried product was exposed to the atmosphere to give the sesquihydrate, 22.9 g (92%). Characterising data were consistent with a standard sample of the title compound.

The invention claimed is:
1. A process for the production of a compound of formula (I), or a pharmaceutically acceptable salt and/or hydrate thereof:

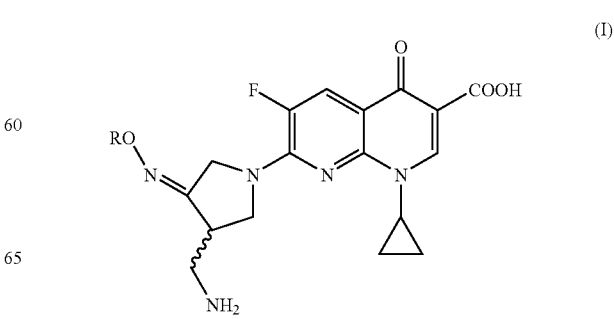

(I)

wherein R is $C_{1-4}$ alkyl or $C_{1-4}$ haloalkyl, which comprises reaction of a compound of formula (II):

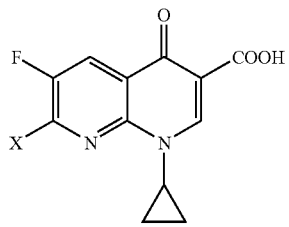
(II)

wherein X is a leaving group; with a compound of formula (III):

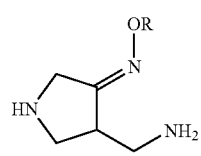
(III)

wherein R is as defined for formula (I), or a salt thereof;
in the presence of a base, wherein the base is triethylamine or a tetra$C_{1-6}$alkylammonium hydroxide, and an aqueous solvent, wherein the solvent is water;
and optionally forming a pharmaceutically acceptable salt and/or hydrate thereof.

2. The process according to claim 1 wherein 10 volumes of solvent based on the compound of formula (II) are used.

3. The process according to claim 1 wherein between 1.01 and 1.08 mole equivalents of the compound of formula (III) based on the compound of formula (II) are used.

4. The process according to claim 1 performed at a temperature between ambient and about 60° C.

5. The process according to claim 1 wherein the base is triethylamine.

6. The process according to claim 1 wherein between 3.2 and 3.8 mole equivalents of base is used based on the compound of formula (II), and wherein the compound of formula (III) is in the form of the dimethanesulfonate salt, the hydrochloride salt, the trifluoroacetate salt, or the sulfate salt.

7. The process according to claim 1 wherein X is chloro.

8. The process according to claim 1 wherein the compound of formula (III) is 4-aminomethyl-3-methoxyiminopyrrolidinium dimethanesulfonate.

9. The process according to claim 1 wherein R is $C_1$ alkyl.

10. The process according to claim 1 wherein the compound of formula (I) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof.

11. A process for the production of a compound of formula (I), or a pharmaceutically acceptable salt and/or hydrate thereof:

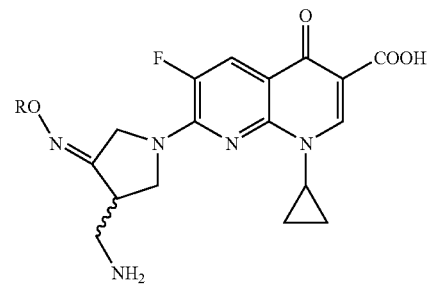
(I)

wherein R is $C_{1-4}$ alkyl or $C_{1-4}$ haloalkyl, which comprises reaction of a compound of formula (II):

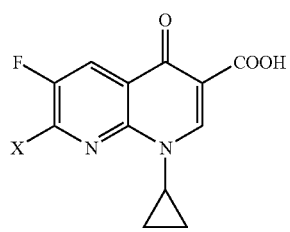
(II)

wherein X is a leaving group; with a compound of formula (III):

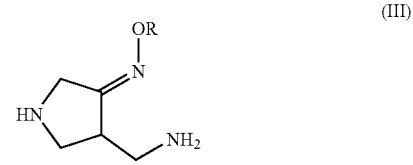
(III)

wherein R is as defined for formula (I), or a salt thereof;
in the presence of a base and an aqueous solvent; wherein the base is a tetra$C_{1-6}$alkylammonium hydroxide;
and optionally forming a pharmaceutically acceptable salt and/or hydrate thereof.

12. The process according to claim 11 wherein the base is tetrabutylammonium hydroxide or tetramethylammonium hydroxide.

13. The process according to claim 11 wherein the solvent is aqueous acetonitrile, an aqueous alcohol or water.

14. The process according to claim 11 wherein when the solvent is aqueous acetonitrile and a ratio of between 0.7 and 1.4 acetonitrile:water is used.

15. The process according to claim 11 wherein the compound of formula (III) is 4-aminomethyl-3-methoxyiminopyrrolidinium dimethanesulfonate.

16. The process according to claim 11 wherein R is $C_1$ alkyl.

17. The process according to claim 11 wherein the compound of formula (I) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof.

* * * * *

UNITED STATES PATENT AND TRADEMARK OFFICE
CERTIFICATE OF CORRECTION

| | | |
|---|---|---|
| PATENT NO. | : 7,232,907 B2 | Page 1 of 1 |
| APPLICATION NO. | : 10/692640 | |
| DATED | : June 19, 2007 | |
| INVENTOR(S) | : John D. Hayler, Hoon Choi and Sungwook Cho | |

It is certified that error appears in the above-identified patent and that said Letters Patent is hereby corrected as shown below:

On the title page, item (63), line 2, "Sep. 1, 1999" should read --Sep. 1, 2000--.

Column 1, line 10, "Sep. 1, 1999" should read --Sep. 1, 2000--.

Signed and Sealed this

Twenty-first Day of August, 2007

JON W. DUDAS
*Director of the United States Patent and Trademark Office*